United States Patent [19]

Wätjen

[11] Patent Number: 5,565,580
[45] Date of Patent: Oct. 15, 1996

[54] GLUTAMATE ANTAGONISTS

[75] Inventor: Frank Wätjen, Herley, Denmark

[73] Assignee: NeuroSearch A/S, Glostrup, Denmark

[21] Appl. No.: 372,598

[22] Filed: Jan. 13, 1995

[30] Foreign Application Priority Data

Jan. 27, 1994 [DK] Denmark .................................. 0114/94

[51] Int. Cl.$^6$ ..................... A61K 31/40; C07D 403/12
[52] U.S. Cl. ............................................................ 548/456
[58] Field of Search ............................. 548/456; 514/422

[56] References Cited

FOREIGN PATENT DOCUMENTS

| 0432648A2 | 6/1991 | European Pat. Off. . |
|---|---|---|
| 55661 | 5/1967 | Germany . |

OTHER PUBLICATIONS

Cerebrovasc. Brain. Metab. Rev., Vol. 6, No. 3, pp. 225–256 (1994).
NeuroReport, vol. 5, No. 8, pp. 877–880 (Apr. 1994).
New Eng. J. Med., vol. 330, No. 9, pp. 613–622 (1994).

*Primary Examiner*—David B. Springer
*Attorney, Agent, or Firm*—Gordon W. Hueschen

[57] ABSTRACT

The present patent application discloses compounds having the formula or a pharmaceutically acceptable salt thereof
wherein
one $R^{21}$ and $R^{22}$ is alkyl and the other is hydrogen or both of $R^{21}$ and $R^{22}$ are hydrogen;
and $R^1$, $R^2$, $R^3$, $R^4$, $R^{11}$, $R^{12}$, $R^{13}$, and $R^{14}$ each independently are hydrogen, halogen, $CF_3$, CN, or $NO_2$; provided that at least one of $R^1$, $R^2$, $R^3$, $R^4$, $R^{11}$, $R^{12}$, $R^{13}$, and $R^{14}$ are different from hydrogen The compounds are useful as in vivo active glutamate antagonists.

6 Claims, No Drawings

GLUTAMATE ANTAGONISTS

The present invention relates to novel excitatory amino acid antagonists, including glutamate antagonists, a method of treatment therewith, pharmaceutical compositions comprising the compounds and to a method of preparing the novel compounds of the invention.

OBJECT OF THE INVENTION

It is an object of the present invention to provide novel excitatory amino acid antagonists, including glutamate and/or aspartate antagonists, which are useful in the treatment of disorders or diseases of a living animal body, including a human, and especially in the treatment of disorders or diseases which are responsive to the antagonization of glutamate and/or aspartate of such a living animal body.

Another object of the present invention is to provide a method of treating disorders or diseases of a living animal body, including a human, responsive to the antagonization of glutamate and aspartate, which comprises administering to a living animal body, including a human, in need thereof a compound of the invention.

A third object of the present invention is to provide novel pharmaceutical compositions for the treatment of disorders or diseases of a living animal body, including a human, responsive to the antagonization of glutamate and aspartate.

Other objects will become apparent hereinafter to any one skilled in the art.

BACKGROUND OF THE INVENTION

Excessive excitation by neurotransmitters can cause the degeneration and death of neurons. It is believed that this degeneration is in part mediated by the excitotoxic actions of the excitatory amino acids (EAA), glutamate and aspartate, at the N-methyl-D-aspartate (NMDA), the 2-amino-3-(3-hydroxy-5-methyl-isoxazol-4-yl)-propionic acid (AMPA) receptor, the quisqualate receptor and the kainate receptor. This excitotoxic action is responsible for the loss of neurons in cerebrovascular disorders such as cerebral ischemia or cerebral infarction resulting from a range of conditions, such as thromboembolic or haemorrhagic stroke, cerebral vasospasm, hypoglycaemia, cardiac arrest, status epilepticus, perinatal asphyxia, anoxia such as from drowning, pulmonary surgery and cerebral trauma as well as lathyrism, Alzheimer's, and Huntington's diseases.

The compounds of the present invention may also be useful in the treatment of schizophrenia, Parkinsonism, epilepsy, anxiety, pain and drug addiction.

Most, if not all antagonists of the excitatory amino acids, including glutamate, as well as glutamate antagonists at the AMPA and/or kainate receptors have demonstrated limited, but still significant in vivo activity, for example as demonstrated by their ability to antagonize AMPA induced convulsions. Therefore there is a still unmet need for the identification of in vivo potent glutamate antagonists.

SUMMARY OF THE INVENTION

The invention then, inter alia, comprises the following, alone or in combination:

A compound having the formula

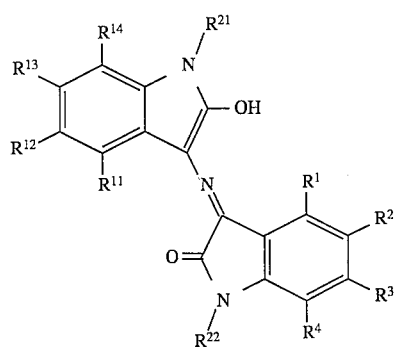

or a pharmaceutically acceptable salt thereof wherein one $R^{21}$ and $R^{22}$ is alkyl and the other is hydrogen or both of $R^{21}$ and $R^{22}$ are hydrogen; and $R^1$, $R^2$, $R^3$, $R^4$, $R^{11}$, $R^{12}$, $R^{13}$, and $R^{14}$ each independently are hydrogen, halogen, $CF_3$, CN, or $NO_2$, provided that at least one of $R^1$, $R^2$, $R^3$, $R^4$, $R^{11}$, $R^{12}$, $R^{13}$, and $R^{14}$ are different from hydrogen;

and a compound as above or a pharmaceutically acceptable salt thereof, wherein $R^{21}$ and $R^{22}$ are each hydrogen, $R^2$, $R^4$, $R^{12}$, and $R^{14}$ are each $NO_2$, and $R^1$, $R^3$, $R^{11}$ and $R^{13}$ are each hydrogen;

and further a method of treating a disorder or disease of a living animal body, including a human, which disorder or disease is responsive to the antagonization of an excitatory amino acid, including glutamate and/or aspartate, which comprises administering to such a living animal body, including a human, in need thereof an effective amount of a compound as identified above;

and a method as above wherein cerebrovascular disorders are treated;

and a method as above wherein Alzheimer's disease, Huntington's disease, schizophrenia, Parkinsonism, epilepsy, anxiety, pain, drug addiction or the degenerative diseases or disorders following cerebral ischemia or cerebral infarction are treated;

and further a pharmaceutical composition comprising a therapeutically-effective amount of a compound as identified above together with at least one pharmaceutically-acceptable carrier;

and further a method for the preparation of a compound as any above, characterized by a) heating a compound having the formula

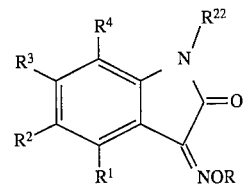

wherein $R^1$, $R^2$, $R^3$, $R^4$, and $R^{22}$ each have the meanings set forth above, and wherein R is alkyl or benzyl b) reacting a compound having the formula

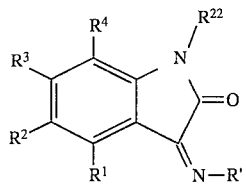

wherein $R^1$, $R^2$, $R^3$, $R^4$ and $R^{22}$ each have the meanings set forth above and R' is alkyl or arylalkyl, with a compound having the formula

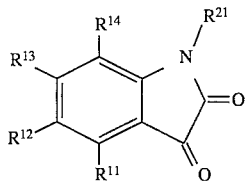

wherein $R^{21}$, $R^{11}$, $R^{12}$, $R^{13}$, and $R^{14}$ each have the meanings set forth above.

Reaction a) above is preferably carried out by heating the ketoxime at temperatures between 220° C. and 250° C. in admixture with $SiO_2$.

Reaction b) above is carried out in a polar solvent, preferentially ethanol. Suitable temperatures for the reaction are between 20° C. and 100° C., depending on the solvent used. The reaction is suitably catalysed by an acid, such as for example acetic acid.

Starting materials for the processes described herein are known or can be prepared from commercially available starting materials by conventional methods (see for example EP-A2-432648). Starting materials for reaction b) can be prepared by reacting the corresponding isatine with a primary alkyl- or arylalkylamine, using the same reaction conditions as for reaction b).

Examples of pharmaceutically-acceptable addition salts include inorganic and organic acid addition salts such as the hydrochloride, hydrobromide, phosphate, sulphate, citrate, lactate, tartrate, maleate, fumarate, mandelate, oxalate, benzoate, ascorbate, cinnamate, benzenesulfonate, methanesulfonate, stearate, succinate, glutamate, salicylate and the acetate. Such salts are formed by procedures well known in the art.

Halogen is fluorine, chlorine, bromine, or iodine; chlorine and bromine are preferred groups.

Alkyl means a straight chained or branched chain of from one to six carbon atoms or cyclic alkyl of from three to seven carbon atoms, including but not limited to, methyl, ethyl, propyl, isopropyl, butyl, isobutyl, t-butyl, pentyl, hexyl, cyclopropyl, cyclobutyl, cyclopentyl, cyclohexyl; methyl, ethyl, propyl and isopropyl are preferred groups.

Aryl means a monocyclic or polycyclic aromatic group, such as for example phenyl and naphthyl.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention exist in (+) and (−) forms as well as in racemic forms. Racemic forms can be resolved into the optical antipodes by known methods, for example, by separation of diastereomeric salts thereof, with an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallization of d- or l(tartrates, mandelates, or camphorsulphonate) salts for example. The compounds of the present invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolution of optical isomers, known to those skilled in the art may be used, and will be apparent to the average man skilled in the art. Such methods include those discussed by J. Jaques, A. Collet, and S. Wilen in "Enantiomers, Racemates, and Resolutions", John Wiley and Sons, New York (1981).

The products of the reactions described herein are isolated by conventional means such as extraction, crystallization, distillation, chromatography, and the like.

Biological Activity

The compounds of the invention exhibit valuable biological properties because of their strong excitatory amino acid (EAA), including glutamate and/or aspartate, antagonizing properties.

In vivo activity (A TPA-induced rigidity)

The selective glutamate receptor agonists at the AMPA(quisqualate) receptor, ATPA, induce rigidity in female NMRI mice at doses between 3 and 15 mg/kg and clonic-tonic seizures and death, probably due to respiratory arrest, at doses between 15 and 40 mg/kg after intravenous (i.v.) administration.

Method: ATPA (2-amino-3-(3-hydroxy-5-tert.butyl-isoxazol-4-yl)-propionic acid) was dissolved in distilled water and test compound was dissolved in a polyoxyl 40 hydrogenated castor oil (5% Cremophor RH™ 40 (BASF)). Test compound was administered either i.v. 5, 30 or 120 min before or p.o. 30 min before an i.v. administration of 15 mg/kg of ATPA to 8 female NMRI mice per dose and the number of mice experiencing rigidity 5 min later was noted. An $ED_{50}$ value was calculated from at least three doses of test compound as the dose inhibiting 50% of the mice from having rigidity.

The compounds of Example 1 exhibit an $ED_{50}$ of 0.1 mg/kg by i.v. administration in this test.

Pharmaceutical Compositions

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) milligrams of active ingredient or, more broadly, one (1) to one hundred (100) milligrams, per tablet, are accordingly suitable representative unit dosage forms.

The compounds of the present invention can be administered in a wide variety of oral and parenteral dosage forms. It will be obvious to those skilled in the art that the following dosage forms may comprise as the active component, either a compound of the invention per se or a pharmaceutically acceptable salt thereof.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carder having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For example, parenteral injection liquid preparations can be formulated as solutions in aqueous polyethylene glycol solution.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

The compounds of this invention are extremely useful in the treatment of central nervous system disorders related to their biological activity. The compounds of this invention may accordingly be administered to a subject, including a human, in need of treatment, alleviation, or elimination of a disorder or disease associated with the biological activity of the compounds of the invention. This includes especially excitatory amino acid dependent, including glutamate and/or aspartate dependent, psychosis, excitatory amino acid dependent, including glutamate and/or aspartate dependent anoxia, excitatory amino acid dependent, including glutamate and/or aspartate dependent ischemia, excitatory amino acid dependent, including glutamate and/or aspartate dependent Parkinsonism, excitatory amino acid dependent, including glutamate and/or aspartate dependent, convulsions and excitatory amino acid dependent, including glutamate and/or aspartate dependent migraine. Suitable dosage ranges are 0.1 to 1000 milligrams daily, 10–500 milligrams daily, and especially 10–100 milligrams daily, dependent as usual upon the exact mode of administration, form in which administered, the indication toward which the administration is directed, the subject involved and the body weight of the subject involved, and further the preference and experience of the physician or veterinarian in charge.

The following nonlimiting examples illustrate the present invention further.

EXAMPLE 1

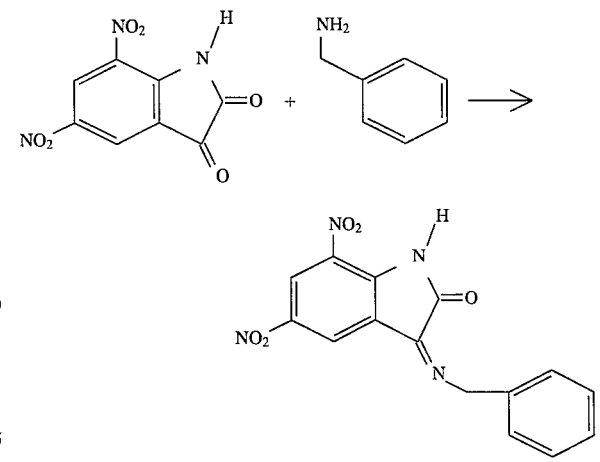

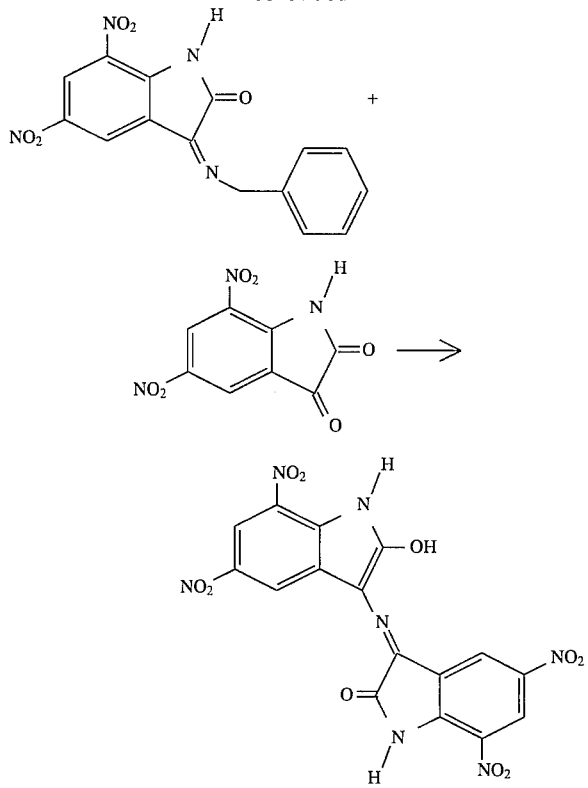

A mixture of 5,7-dinitro-indole-2,3-dione (1.2 g), benzyl amine (3 ml) and acetic acid (3.4 ml) was refluxed in abs. ethanol (30 ml) for 20 min. The mixture was then cooled to ambient temperature, and the precipitate was removed by filtration. This left 0.8 g of the product as a dark solid, which was washed with ethanol. Mp.>300° C. 1-H NMR (500 MHZ, D-6-DMSO: ∂=8.1 ppm(S broad, 1H), 8.4 ppm(S, 1H).

The mono N-methyl analogue having the formula

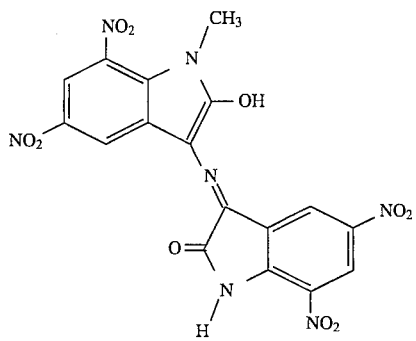

was prepared in exactly the same manner from an equimolar mixture of 5,7-dinitro-1 methyl-indole-2,3-dione and 5,7-dinitro-indole-2,3-dione and benzylamine. The precipitated solid which contained the product as well as the di N-methyl analogue was purified to give the mono N-methyl compound of the invention by column chromatography on silica gel with methanol/ethyl acetate (1/10) as eluent.

I claim:

1. A compound having the formula

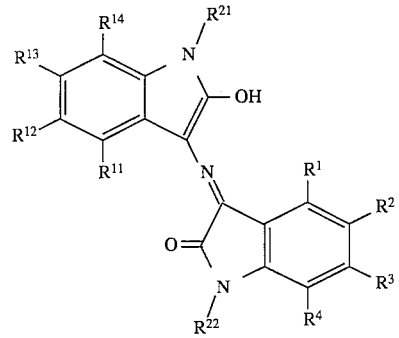

or a pharmaceutically acceptable salt thereof
wherein
one of $R^{21}$ and $R^{22}$ is $C_1$–$C_6$ alkyl or $C_3$–$C_7$ cycloalkyl and the other is hydrogen or both of $R^{21}$ and $R^{22}$ are hydrogen;

and $R^1$, $R^2$, $R^3$, $R^4$, $R^{11}$, $R^{12}$, $R^{13}$, and $R^{14}$ each independently are hydrogen or $NO_2$, provided that two of $R^1$, $R^2$, $R^3$, $R^4$, and that two of $R^{11}$, $R^{12}$, $R^{13}$, and $R^{14}$ are $NO_2$.

2. A compound of claim 1 or a pharmaceutically acceptable salt thereof, wherein $R^{21}$ and $R^{22}$ are each hydrogen, $R^2$, $R^4$, $R^{12}$, and $R^{14}$ are each $NO_2$, and $R^1$, $R^3$, $R^{11}$ and $R^{13}$ are each hydrogen.

3. A method of treating a disorder or disease of a living animal body, including a human, which disorder or disease is responsive to the antagonization of the excitatory amino acid, glutamate which comprises administering to such a living animal body, including a human, in need thereof an effective amount of a compound of claim 1.

4. The method of claim 3 wherein a cerebrovascular disorders is treated.

5. The method of claim 3 wherein Alzheimer's disease, Huntington's diseases, schizophrenia, Parkinsonism, epilepsy, anxiety, pain, drug addiction or a degenerative disease or disorder following cerebral ischemia or cerebral infarction is treated.

6. A pharmaceutical composition comprising a therapeutically-effective amount of a compound of claim 1 together with at least one pharmaceutically-acceptable carrier.

* * * * *

UNITED STATES PATENT AND TRADEMARK OFFICE
CERTIFICATE OF CORRECTION

PATENT NO. : 5,565,580
DATED : Oct. 15, 1996
INVENTOR(S) : Frank Watjen

It is certified that error appears in the above-indentified patent and that said Letters Patent is hereby corrected as shown below:

Title Page, [75], Inventor: "Herley" should read
    -- Herev --.

Title Page, [56], OTHER PUBLICATIONS: Insert as fourth (4th) publication -- Therapeutic opportunities in modulators of excitatory amino acid-mediated neurotransmission, In: P. Krogsgaard-Larsen, J.J. Hansen, eds Excitatory Amino Acid Receptors, Design of Agonists and Antagonists, pages 352-375 (Ellis Horwood, 1993) --

Column 1, line 31: "any one" should read -- anyone --.

Column 4, line 5: "I(tartrates," should read
    -- 1-(tartrates, --.

Column 4, line 30: "(A TPA" should read -- (ATPA --.

UNITED STATES PATENT AND TRADEMARK OFFICE
CERTIFICATE OF CORRECTION

PATENT NO. : 5,565,580
DATED : Oct. 15, 1996
INVENTOR(S) : Frank Watjen

It is certified that error appears in the above-indentified patent and that said Letters Patent is hereby corrected as shown below:

Column 5, line 22: "carder" should read -- carrier --.

Column 8, line 42: "acid, glutamate" should read -- acid glutamate, --.

Column 8, line 46: "disorders" should read -- disorder --.

Signed and Sealed this

Eighteenth Day of March, 1997

Attest:

BRUCE LEHMAN

*Attesting Officer*       *Commissioner of Patents and Trademarks*